United States Patent [19]

Takemura et al.

[11] 4,390,025

[45] Jun. 28, 1983

[54] ULTRASONIC DISPLAY APPARATUS HAVING MEANS FOR DETECTING THE POSITION OF AN ULTRASONIC PROBE

[75] Inventors: Yasuhiko Takemura, Tochigi; Kazuyoshi Saito, Yaita, both of Japan

[73] Assignee: Tokyo Shibaura Denki Kabushiki Kaisha, Kawasaki, Japan

[21] Appl. No.: 255,178

[22] Filed: Apr. 17, 1981

[30] Foreign Application Priority Data

Apr. 24, 1980 [JP] Japan .................................. 55-53482

[51] Int. Cl.³ .............................................. A61B 5/00
[52] U.S. Cl. ....................................... 128/660; 73/620; 128/661
[58] Field of Search .................. 128/660, 663; 73/601, 73/620, 625, 626, 861.25

[56] References Cited

U.S. PATENT DOCUMENTS

| | | | |
|---|---|---|---|
| 4,010,634 | 3/1977 | Baumgortner | 73/620 |
| 4,062,237 | 12/1977 | Fox | 73/861.25 |
| 4,141,347 | 2/1979 | Green et al. | 73/627 |
| 4,200,885 | 4/1980 | Hofstein | 128/660 |
| 4,209,022 | 6/1980 | Dory | 73/626 |
| 4,236,221 | 11/1980 | Cribbs et al. | 128/660 |
| 4,249,539 | 2/1981 | Vilkomerson et al. | 128/660 |

Primary Examiner—Richard J. Apley
Assistant Examiner—George Yanulis
Attorney, Agent, or Firm—Finnegan, Henderson, Farabow, Garrett & Dunner

[57] ABSTRACT

An ultrasonic apparatus including apparatus for detecting the position of an ultrasonic probe, a memory for storing the positions of the ultrasonic probe relative to a reference point in symbolized pattern of a human body, a memory for storing tomogram signals received by the probe relative to the stored positions timing pulse generator apparatus for reading out the stored signals, and apparatus for displaying the symbolized pattern, the position of the probe and the relative tomogram data simultaneously on the screen of a monitor. The position detecting apparatus includes auto-reset circuits for arbitrarily resetting the position of the probe in the memory to the reference point regardless of the actual position of the probe.

7 Claims, 5 Drawing Figures

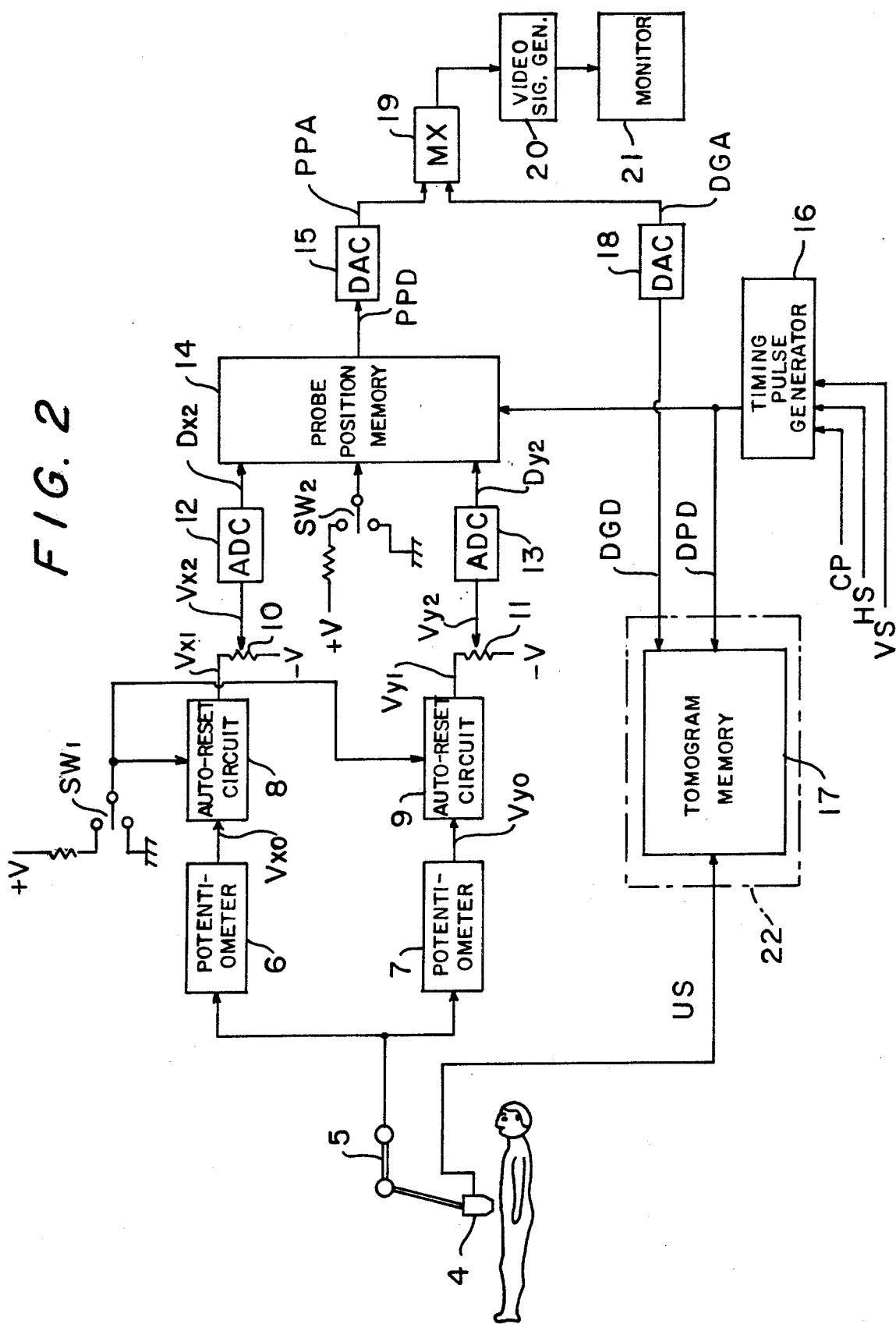

FIG. 4
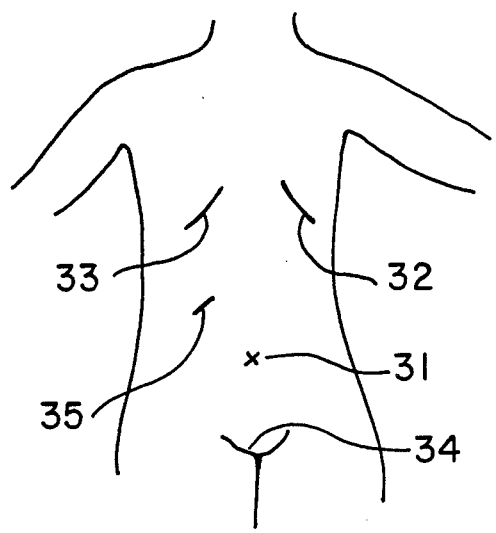
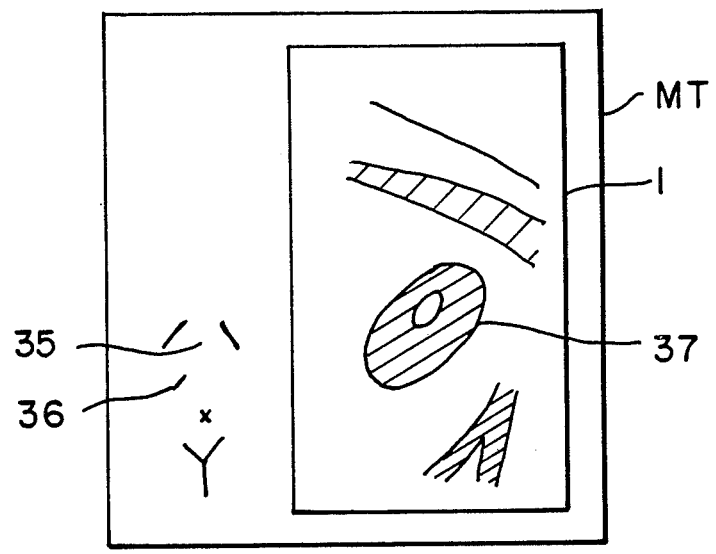

ULTRASONIC DISPLAY APPARATUS HAVING MEANS FOR DETECTING THE POSITION OF AN ULTRASONIC PROBE

BACKGROUND OF THE INVENTION

This invention relates to an ultrasonic diagnosis apparatus, and particularly to an ultrasonic diagnosis apparatus capable of simultaneously depicting a human body in a symbolized pattern, a mark showing an ultrasonic probe position on the body and an ultrasonic tomograph on a display.

Recently, an increase in the functions of ultrasonic diagnosis apparatus has been remarked with the development of ultrasonic diagnosis techniques. Especially, apparatus is used which has the function of displaying ultrasonic images on a monitor displaying screen which also depicts adjacent the images a human body in a symbolized pattern having an ultrasonic probe position mark. Such a tomogram gives a simultaneous record of the ultrasonic probe position and the diagnosis portion which is clinically extremely convenient in the case of recording the ultrasonic image.

As shown in FIG. 1, an ultrasonic image 1 including a tomograph 1a is depicted on a monitor displaying screen MT while also showing simultaneously the human body in a symbolized pattern 2 and the ultrasonic probe position 3 on the human body neighboring with the image 1.

However, there is a shortcoming in the prior art that the position of the ultrasonic probe may be inaccurately displayed because the movement of the ultrasonic probe is not directly observed to display its position, but an operator indirectly writes the ultrasonic probe position on the human body symbolized pattern by a switch, for example a joy stick, on an operating panel.

SUMMARY OF THE INVENTION

It is accordingly one object of this invention to provide an ultrasonic diagnosis apparatus, wherein the position of an ultrasonic probe, i.e., the scanning position, can be accurately displayed against each portion of a subject, as determined by the apparatus.

It is another object of the invention to improve ultrasonic diagnosis apparatus, wherein an accurate symbolized pattern of the human body according to the subject can be simultaneously displayed with an ultrasonic tomogram.

It is yet another object of the invention to provide ultrasonic diagnosis apparatus, wherein the human body symbolized pattern can be depicted with a locus, as determined by the apparatus.

Briefly, these and other objects are achieved in accordance with a first aspect of the invention, by an ultrasonic diagnosis apparatus wherein an ultrasonic tomogram and symbolized pattern of a human body are simultaneously displayed on the screen of a monitor. The ultrasonic diagnosis apparatus also includes an ultrasonic probe position-detecting apparatus, a first memory, a second memory, a timing pulse generating apparatus, and apparatus for displaying the information stored in the memories on the screen.

The position-detecting apparatus detects the locus of an ultrasonic probe in an X-Y two-dimensional plane relative to a reference point. The first memory has memory regions corresponding to specific areas of the symbolized pattern of the body and for storing a signal representing at least a specific one of the ultrasonic probe's loci as a reference point for the position-detecting apparatus. The second memory stores ultrasonic tomogram signals obtained by the ultrasonic probe at the addresses as defined by the position-detecting apparatus. The timing pulse generating apparatus reads out the signals stored in the first and second memories to a monitor screen for simultaneously displaying on the screen the ultrasonic signals reflected to an ultrasonic probe and at the precise position of the probe as shown on the symbolized pattern of the human body.

BRIEF DESCRIPTION OF THE DRAWINGS

FIG. 2 is a schematic block diagram to illustrate the structure of the preferred embodiment of this invention.

FIG. 4(a) is a pictorial view of assistance in explaining the operation of FIG. 2; and FIG. 4(b) is a schematic elevation to illustrate the image on the displaying screen of FIG. 2.

DESCRIPTION OF THE PREFERRED EMBODIMENTS

Figure 1:
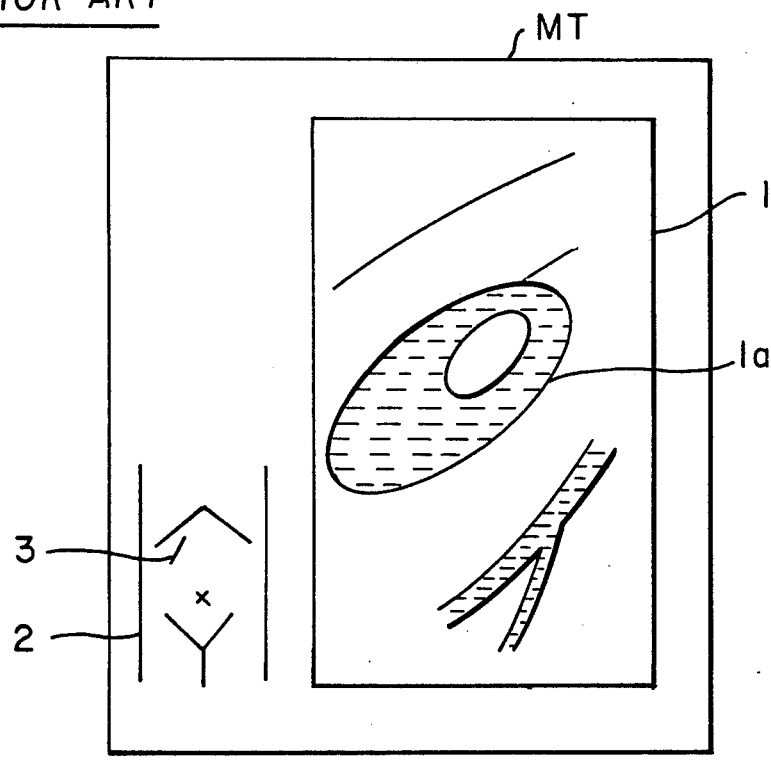
FIG. 1 is a schematic elevation to illustrate the image on the displaying screen of a conventional ultrasonic diagnosis apparatus.

We will now describe an embodiment of this invention by referring to the drawings.

Figure 3:
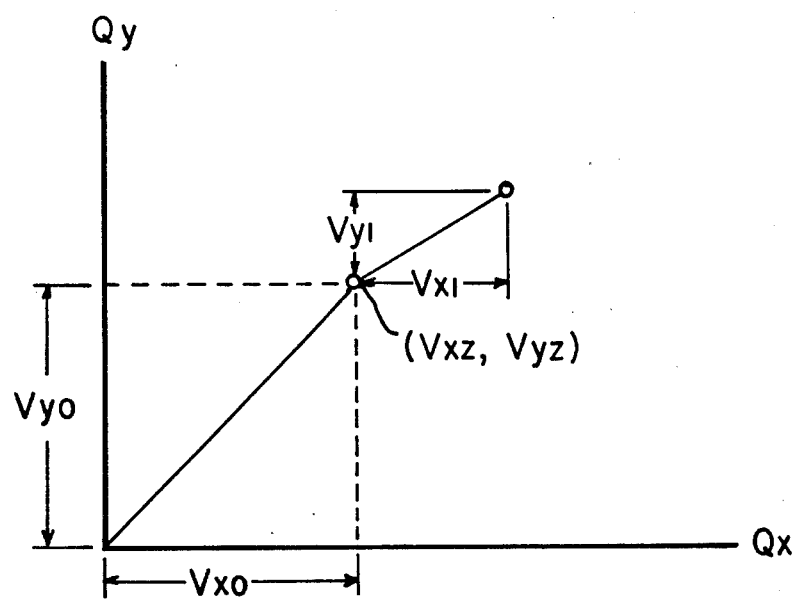
FIG. 3 is a graphic representation of assistance in explaining the operation of FIG. 2.

In FIG. 2, an ultrasonic probe 4, for example, a linear electronic scan probe shown as scanning portions of a subject such as a human body emits ultrasonic signals into the subject and receives ultrasonic echo signals US from the subject to generate outputs. The ultrasonic probe 4 is supported by a support rod 5 which is able to move freely in the X-axis direction and Y-axis direction of a two-dimensional plane. Potentiometers 6 and 7 respectively generate voltage signals Vxo and Vyo (also shown in FIG. 3) corresponding to the absolute move amount Qx in the X-axis direction and the absolute move amount Qy in the Y-axis direction of the two-dimensional plane of movement of the support rod 5.

Auto-reset circuits 8 and 9 respectively generate predetermined initial voltages Vxz and Vyz representing the predetermined reference point, or point of origin, of the probe 4, when a switch SW1 is set on a ground potential contact. Circuits 8 and 9 also respectively generate voltage signals Vx1 and Vy1 corresponding to the changed values in the output voltage signals Vxo and Vyo generated by the potentimeters 6 and 7 reflecting the movement of the probe 4 from the reference point in the X and Y directions as will be explained in detail hereinafter.

Variable resistors 10 and 11 respectively adjust the output voltage signals of the auto-reset circuits 8 and 9 to the desired levels. For example, assuming that the reference point is the human navel, after positioning the probe 4 on the navel, the resistors 10 and 11 may be manually adjusted to reflect properly the position of the probe.

Analog-to-digital convertors (ADC) 12 and 13 respectively convert the output voltage signals Vx2 and Vy2 from the variable resistors 10 and 11 to the digital signals Dx2 and Dy2 to generate address signals for a probe position memory 14.

The probe position memory 14 contains memory addresses respectively corresponding to specific image elements on a monitor display screen 21. The individual addresses designated by the output signals Dx2 and Dy2 of the ADC's 12 and 13 are written into the memory 14, or not, by the signal of the logic "1" or "0" as actuated by a manual switch SW2.

A digital-to-analog convertor (DAC) 15 converts the output signal PPD of the probe position memory 14 to an analog signal PPA to generate an output.

A timing pulse generator 16 generates image element position signals DPD corresponding for each image element position in the monitor display screen according to clock pulses CP corresponding to each image element, horizontal synchronizing signals HS and vertical synchronizing signals VS. A tomograph image memory 17 included in control apparatus 22 of the ultrasonic diagnosis apparatus stores the ultrasonic echo signals US generated from the ultrasonic probe 4 to the address designated by the image element position signal DPD as a tomograph image signal, thus having memory addresses corresponding to each image element in the monitor display screen.

A digital-to-analog convertor (DAC) 18 converts the tomograph image signals DGD read out from the tomogram memory 17 to analog signals DGA, and a mixer 19 mixes the output signal PPA of the DAC 15 and the output signal DGA of the DAC 18 to generate an output. A video signal generator 20 converts the output signal of the mixer 19 to the video signal, and the monitor 21 displays the tomograph image, the symbolized patterns of the human body as well as the scan position of the ultrasonic probe 4 on the CRT display screen.

Furthermore, the human body symbolized pattern is stored in the probe position memory 14 for showing the locus of the ultrasonic probe 4 while tracing relevant parts of the human body. Also, preferably, the manual switch SW2 for controlling the writing operation of the probe position memory 14 is located in the vicinity of the probe 4 for easy access by the operator of the probe.

Next, we will describe the operation of the ultrasonic diagnosis apparatus constructed as described above.

First, in this apparatus, the human body symbolized pattern as to a patient is written in the probe position memory 14 as the locus of the ultrasonic probe 4 by tracing the objective parts of the patient's body before obtaining the tomogram of the patient. In this case, as shown in FIG. 4(a), the navel 31 is elected as the reference point of the human body symbolized pattern. Then with the ultrasonic probe 4 put on the navel position the operator of the probe sets the moveable contact of the switch SW1 to the earth side to reset the auto-reset circuits 8 and 9 with the predetermined initial voltages Vxz and Vyz respectively. The voltages Vxz and Yxz are respectively converted to the digital values for the address signals of the probe position memory 14 by the ADCs 12 and 13 after being adjusted to the desired levels by the variable resistors 10 and 11.

At this time, the signal of logic "1" is written in the address of the probe position memory 14 corresponding to the initial voltages Vxz and Vyz by manually setting the moveable contact of the switch SW2 to the voltage source +V side. In other words, the signal of the logic "1", i.e., the signal representing the position of the navel in this case, is written in the address of the probe position memory 14 corresponding to the initial voltages Vxz and Vyz, when the switch SW2 is actuated after the switch SW1 is set to ground. If the address is adjusted by the variable resistors 10,11, the address of the signal representing the position of the navel becomes ($Vxz \times \alpha$, $Vyz \times \beta$) wherein the adjusting ratios set by the variable resistors 10 and 11 are $\alpha\%$ and $\beta\%$ respectively, for the output voltage signals of the auto reset circuits 8 and 9. It is, therefore, possible to freely alter the written address of the signal representing the reference point into another arbitrary address by changing the level adjusting ratios with the variable resistors 10 and 11.

When the signal representing the navel reference point has been written into the probe position memory 14, the movable contact of the switch SW2 is set on the earth potential side to avoid confusing logic signals if the probe is moved. Of course, when the position of the probe is to be recorded, the moveable contact of the switch SW2 is set back on the +V side. At the moment that the timing pulse generator circuit recognizes coincidence between the position of the probe 4 and a body position stored in the tomogram, signals PPD and DGD of memory 17 are issued from the probe position memory 14 and the tomogram memory 17 to DAC 15 and DAC 18 respectively. The resulting analog signals are transmitted to the video signal generator 20 through the mixer 19. Thus, the point signals to represent the reference point, i.e., the navel, are displayed at the image element coordinate position corresponding to ($Vxz \times \alpha$, $Vyz \times \beta$) of the displaying screen in the monitor 21. Here, if the reference point of the navel is displayed on the monitor 21 is not precisely positioned, it will be shifted to the desired position by adjusting the level ratio of the variable resistors 10 and/or 11.

After the position of the navel is properly determined on the human body symbolized pattern and written into the probe position memory 14, the ultrasonic probe 4 will be moved from the reference position and the movable contact of the switch SW2 will be returned to the voltage source +V side to trace the outlines of the human body which are necessary to obtain the desired symbolized pattern. For example, as shown in FIG. 4(a), there will be traced the boundary lines 32 and 33 between the chest and belly, and the boundary line 34 of the underbelly.

It should be noted that when moving the ultrasonic probe 4 from the boundary line 32 to the boundary line 33 or from the boundary line 33 to the boundary line 34, loci of the ultrasonic probe 4 unnecessary for the diagnosis will not be written in the probe position memory 14 if the movable contact of the switch SW2 is set on the earth potential side. On the other hand, in the process of tracing each portion 32, 33 or 34 shown in FIG. 4(a), the movable contact of the switch SW2 must be set to the source +V side, in order for the signals of the logic "1" to be written on the probe position memory 14 corresponding to the locus of the ultrasonic probe 4. The written signals representing the portions of the human body are then successively read out as the image element position signals DPD generated from the timing pulse generator 16 and displayed on the displaying screen of the monitor 21 as the symbolized pattern.

After the human body symbolized pattern has been written in the probe position memory 14, the signal representing the objective portion of the body is written as to the symbolized pattern in the same way. Ultrasonic sound waves are then transmitted from the ultrasonic probe 4 to develop the ultrasonic echo signals US from the objective portion on the tomogram memory 17. The timing pulse generator 16 can synchronously read out the image element position signals DPD as to the human body symbolized pattern and the signal representing the objective position which are written in the probe position memory 14 and the tomogram signals written in the tomogram memory 17. The output signals PPD from the probe position memory 14 and the output signals DGD from the tomogram memory 17 are respectively converted to analog signals PPA and DGA by the DAC 15 and 18 and mixed by the mixer 19. The mixed signal is converted to a video signal by a video signal generator 20, as shown in FIG. 4(b), displayed on the depicting screen MT of the monitor 21. As a result, the human body symbolized pattern 35, the objective position 36, i.e., the ultrasonic probe's position, and the ultrasonic tomogram are shown simultaneously on the screen MT of the monitor 21, as shown in FIG. 4b.

Since the symbolized pattern of the human body is obtained by tracing the necessary body portions with respect to the patient's navel, the symbolized pattern itself directly relates to the physical features of the individual patient and the relative objective position is displayed accurately for purposes of clinical analysis.

Moreover, with the ultrasonic diagnosis apparatus of the invention, it is possible to move the writing address of the signal representing the reference point to another arbitrary position by altering the adjusting ratios $\alpha$ and $\beta$ of the signal level by adjusting the variable resistors 10 and 11.

What is claimed is:

1. An ultrasonic diagnosis apparatus including an ultrasonic probe, wherein an ultrasonic tomogram and a planar symbolized pattern of a human body are simultaneously displayed on the screen of a monitor, said ultrasonic diagnosis apparatus comprising:

means for detecting a predetermined number of positions of the ultrasonic probe in a two-dimensional plane relative to a reference point in the plane, and for generating signals identifying said position, said position-detecting means including auto-reset circuit means for generating a predetermined standard voltage identifying said reference point regardless of the position of said ultrasonic probe;

first memory means for storing said symbolized pattern, said reference point and said predetermined positions with respect to said symbolized pattern, and said signals generated by said position detecting apparatus;

second memory means for storing ultrasonic tomogram signals received by said ultrasonic probe relative to said predetermined positions;

timing pulse generating apparatus for simultaneously reading out said stored information from said first and second memory means as to the detected positions of said probe; and means for simultaneously displaying on said screen the position of said probe relative to said symbolized pattern and the tomogram relative to the probe position reflecting said read-out information.

2. The ultrasonic diagnosis apparatus of claim 1 wherein said position-detecting means includes variable resistors for adjusting the output of the auto-reset circuit means to a desired value.

3. The ultrasonic diagnosis apparatus of claim 1 also including means for selectively preventing the storage of said detected positions of said probe in said first memory means.

4. The ultrasonic diagnosis apparatus of claim 2 or 3 wherein said detecting means also includes analog-to-digital convertors for processing the outputs of said variable resistors before storage on said first memory means.

5. The ultrasonic diagnosis apparatus of claim 1 wherein said displaying means also includes digital-to-analog convertors for processing said information read out from said first and second memory means.

6. The ultrasonic diagnosis apparatus of claim 5 wherein said displaying means also includes a mixer and a video signal generator for successively processing the outputs of said digital-to-analog convertors for display of said information on said screen.

7. An ultrasonic diagnosis apparatus including an ultrasonic probe wherein an ultrasonic tomogram and a symbolized pattern of a human body are simultaneously displayed on the screen of a monitor, said ultrasonic diagnosis apparatus comprising:

a position-detecting apparatus for detecting the relative locus of the ultrasonic probe by image element positions in an X-Y two-dimensional plane against a reference point, and for generating signals identifying the detected position, said position-detecting apparatus including auto-reset circuit means for generating a predetermined standard voltage identifying said reference point regardless of the positions of said ultrasonic probe;

a memory having a capacity at least corresponding specifically to the data required by the screen of the monitor in image element positions;

first means for writing said signals representing the detected loci of the ultrasonic probe in the storing region of the symbolized pattern in said memory;

second means for writing ultrasonic tomogram signals obtained by the ultrasonic probe in another region of the memory;

a timing pulse generating means for reading out said signals stored in the memory by the signals corresponding to each image element position on the screen of the monitor; and a displaying apparatus for simultaneously displaying the read out signals on the screen of the monitor.

* * * * *